United States Patent
Esksuri et al.

(10) Patent No.: US 7,959,584 B2
(45) Date of Patent: Jun. 14, 2011

(54) DEDICATED DISTAL PROTECTION GUIDEWIRES

(75) Inventors: Alan D. Esksuri, Hanover, MN (US); James G. Hansen, Coon Rapids, MN (US); Brian J. Lowe, Zimmerman, MN (US); John M. K. Daniel, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1735 days.

(21) Appl. No.: 10/159,079

(22) Filed: May 29, 2002

(65) Prior Publication Data
US 2003/0225418 A1 Dec. 4, 2003

(51) Int. Cl.
*A61M 25/00* (2006.01)
*A61M 5/178* (2006.01)

(52) U.S. Cl. .................. 600/585; 604/164.13

(58) Field of Classification Search .................. 600/300, 600/585; 604/164.01, 164.13, 165.01, 165.02, 604/170.01, 164.02; 606/191, 198, 200, 606/108, 194, 195
See application file for complete search history.

(56) References Cited

U.S. PATENT DOCUMENTS

| | | | |
|---|---|---|---|
| 3,472,230 | A | 10/1969 | Fogarty |
| 3,952,747 | A | 4/1976 | Kimmell, Jr. |
| 3,996,938 | A | 12/1976 | Clark, Iii |
| 4,046,150 | A | 9/1977 | Schwartz et al. |
| 4,425,908 | A | 1/1984 | Simon |
| 4,554,929 | A * | 11/1985 | Samson et al. ............... 600/585 |
| 4,590,938 | A | 5/1986 | Segura et al. |
| 4,606,347 | A * | 8/1986 | Fogarty et al. ............... 606/194 |
| 4,619,246 | A | 10/1986 | Molgaard-Nielsen et al. |
| 4,650,466 | A | 3/1987 | Luther |
| 4,706,671 | A | 11/1987 | Weinrib |

(Continued)

FOREIGN PATENT DOCUMENTS
DE 28 21 048 7/1980
(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner* — Anu Ramana
(74) *Attorney, Agent, or Firm* — Seager, Tufte & Wickhem LLC

(57) ABSTRACT

A dedicated distal protection guidewire having proximal and distal stops disposed about an elongated core wire is disclosed. A guidewire in accordance with the present invention includes an elongated core wire having a relatively stiff proximal section and a relatively flexible distal section, a distal stop disposed about a portion of the elongated core wire, and a proximal stop disposed about a portion of the elongated core wire proximal the distal stop. The distal stop may be formed from an enlarged outer diameter portion on the elongated core wire, or may be formed from an object disposed about and secured to a portion of the elongated core wire. The proximal stop may include an O-ring disposed within a recessed surface on the elongated core wire, or an annular ring having several circumferentially disposed notches. In one exemplary embodiment, a distal protection guidewire may include a proximal stop comprising a first tubular member, a second tubular member, and a plurality of expandable struts actuatable between a collapsed position and a deployed position.

32 Claims, 6 Drawing Sheets

U.S. PATENT DOCUMENTS

| | | | |
|---|---|---|---|
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,944,729 A * | 7/1990 | Buckberg et al. | 604/164.02 |
| 4,969,891 A | 11/1990 | Gewertz | |
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,167,239 A * | 12/1992 | Cohen et al. | 600/585 |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,376,100 A | 12/1994 | Lefebvre | |
| 5,421,832 A | 6/1995 | Lefebvre | |
| 5,423,742 A | 6/1995 | Theron | |
| 5,449,372 A | 9/1995 | Schmaltz et al. | |
| 4,842,579 A | 10/1995 | Shiber | |
| 5,456,667 A | 10/1995 | Ham et al. | |
| 5,462,529 A | 10/1995 | Simpson et al. | |
| 5,465,733 A | 11/1995 | Hinohara et al. | |
| 5,505,699 A * | 4/1996 | Forman et al. | 604/103.09 |
| 5,536,242 A | 7/1996 | Willard et al. | |
| 5,549,626 A | 8/1996 | Miller et al. | |
| 5,551,444 A | 9/1996 | Finlayson | |
| 5,637,089 A * | 6/1997 | Abrams et al. | 604/95.01 |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,817,101 A * | 10/1998 | Fiedler | 623/1.11 |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,984,878 A * | 11/1999 | Engelson | 600/585 |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,050,972 A * | 4/2000 | Zadno-Azizi et al. | 604/97.01 |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,623 A * | 5/2000 | Zadno-Azizi et al. | 604/530 |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,132,388 A * | 10/2000 | Fleming et al. | 600/585 |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,165,292 A * | 12/2000 | Abrams et al. | 148/563 |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,322,572 B1 | 11/2001 | Lee | |
| 6,336,934 B1 * | 1/2002 | Gilson et al. | 606/200 |
| 6,344,049 B1 | 2/2002 | Levinson et al. | |
| 6,355,014 B1 * | 3/2002 | Zadno-Azizi et al. | 604/99.02 |
| 6,443,926 B1 * | 9/2002 | Kletschka | 604/96.01 |
| 6,533,751 B2 * | 3/2003 | Cragg et al. | 604/93.01 |
| 6,551,341 B2 * | 4/2003 | Boylan et al. | 606/200 |
| 6,602,272 B2 * | 8/2003 | Boylan et al. | 606/200 |
| 2001/0012951 A1 | 8/2001 | Bates et al. | |
| 2002/0026213 A1 | 2/2002 | Gilson et al. | |
| 2002/0062092 A1 | 5/2002 | Muni et al. | |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |

| | | |
|---|---|---|
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 0 982 046 A1 | 1/2000 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular* Device Update, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," *AJR*, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," *The New England Journal of Medicine*, 339(10):659-666 (Sep. 1988).

Jordan, Jr. et al., "Microemboli Detected by Transcranial Doppler Monitoring . . . ," Cardiovascular Surgery, 7(1)33-38 (Jan. 1999).

Lesh, "Can Catheter Ablation Cure Atrial Fibrilllation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," American Heart Journal 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, *The* Journal of Invasive Cardiology, 8(E):25E-30E (1996).

\* cited by examiner

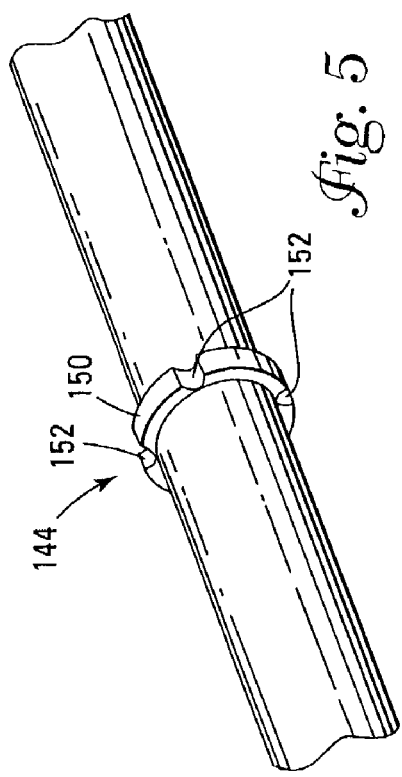
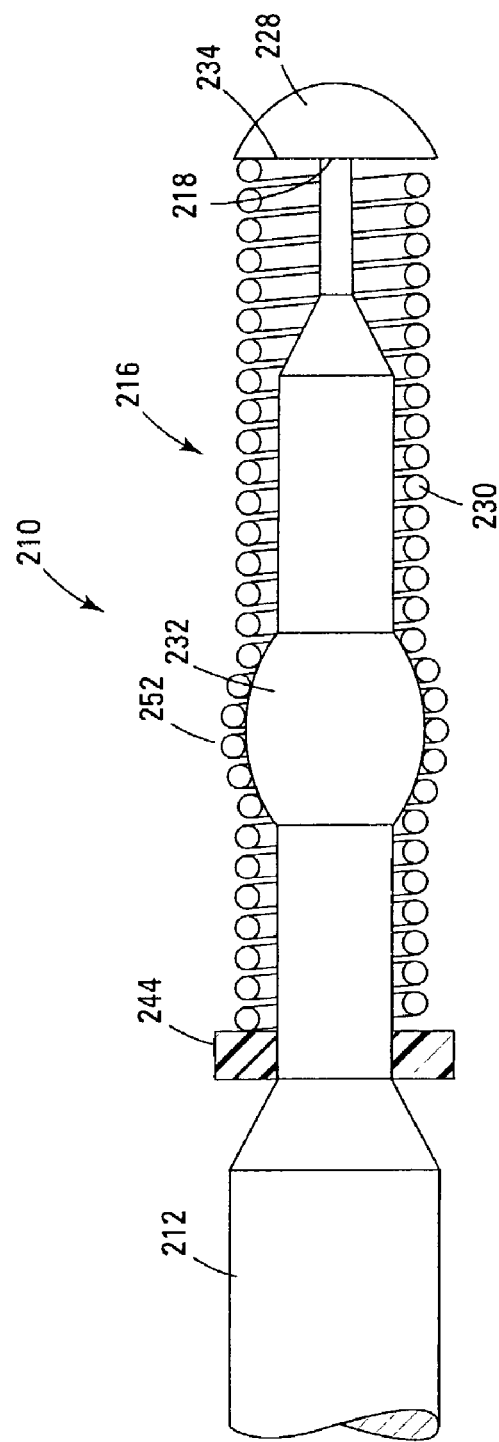

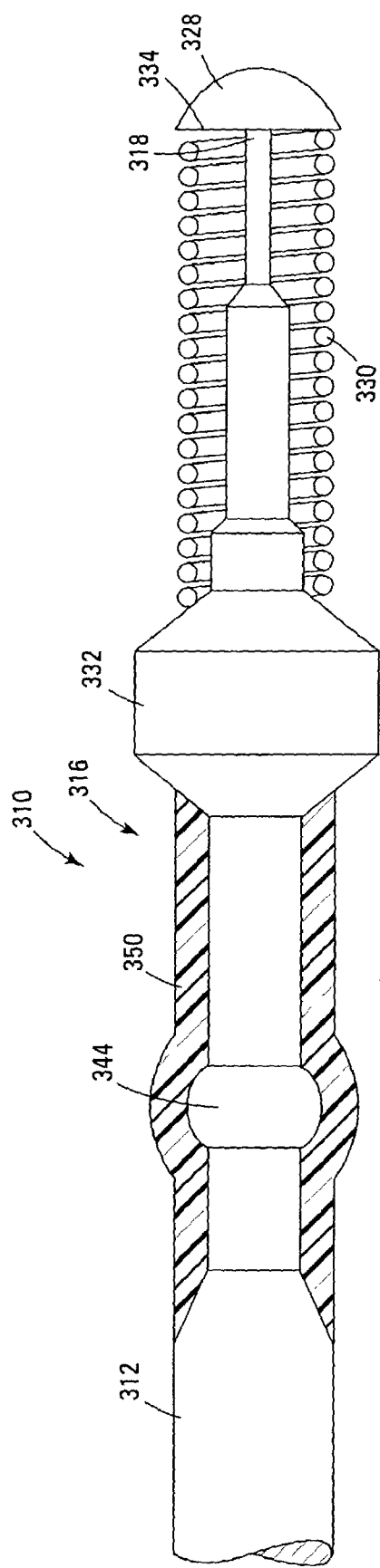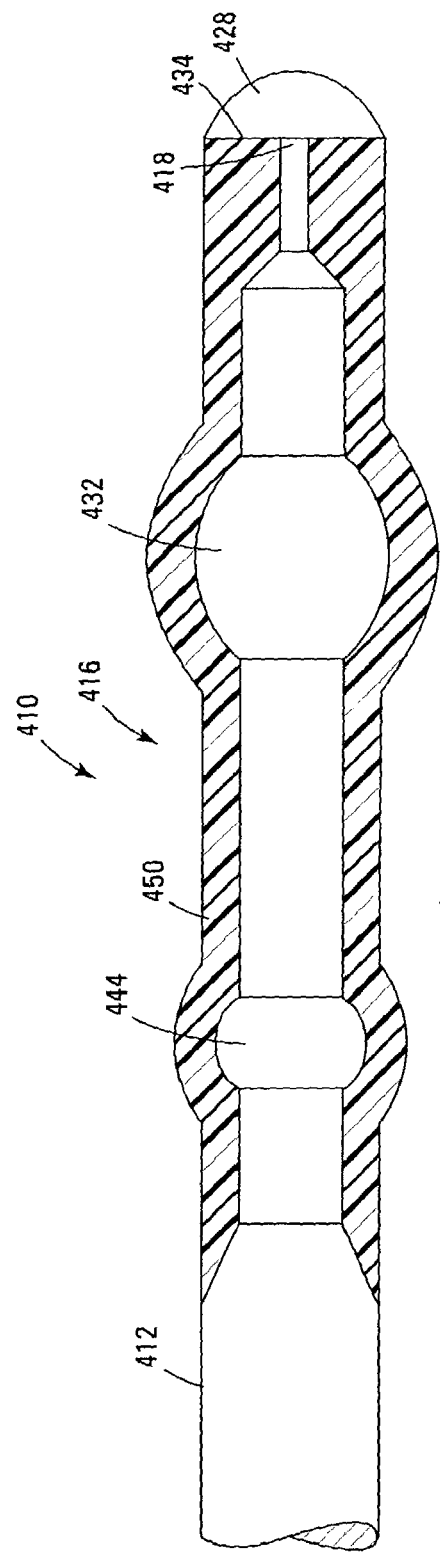
Fig. 7
Fig. 8

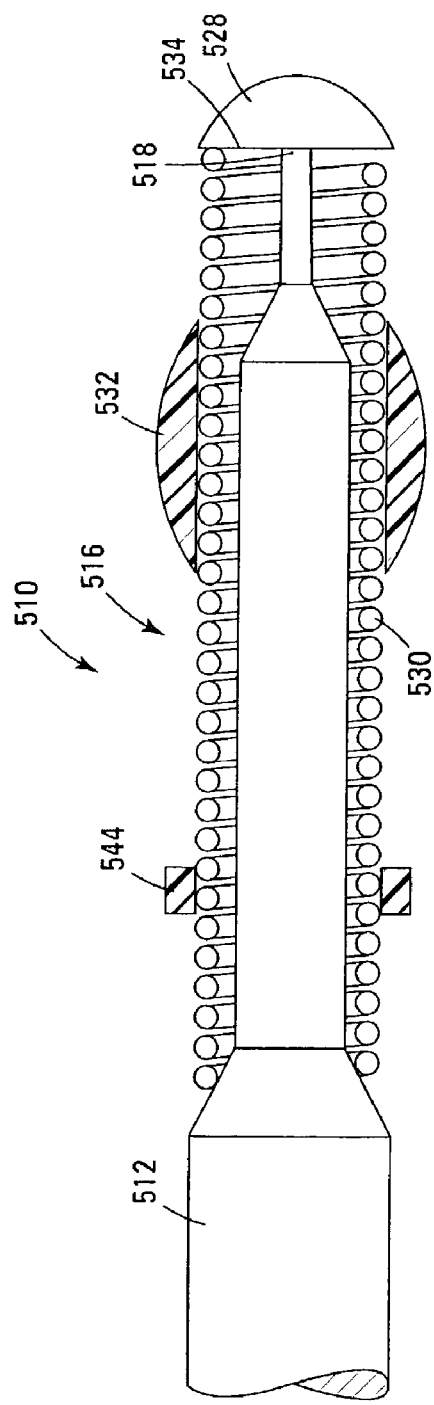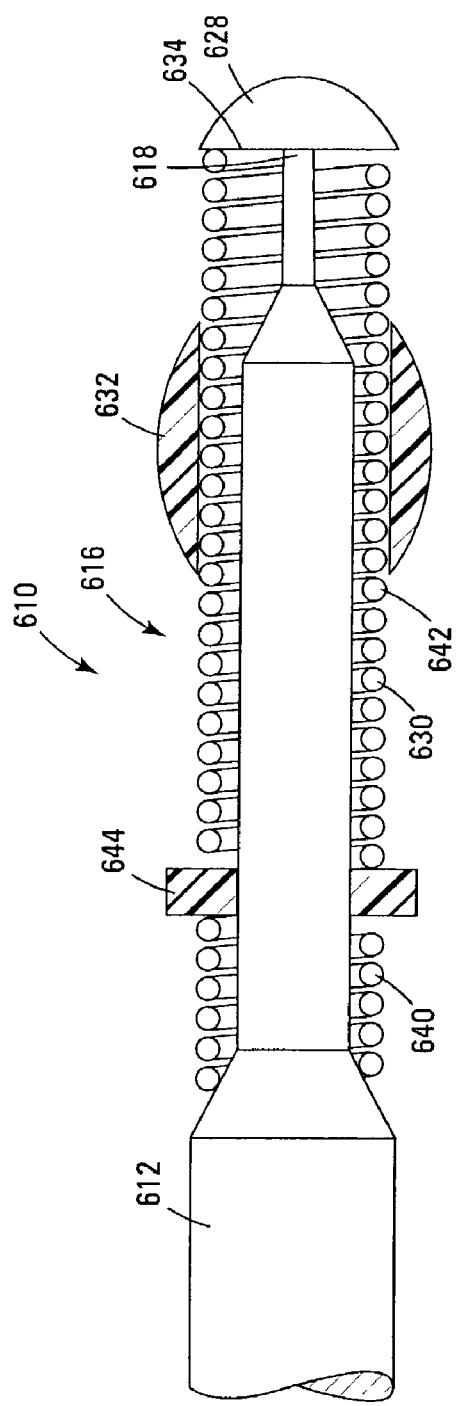
Fig. 9
Fig. 10

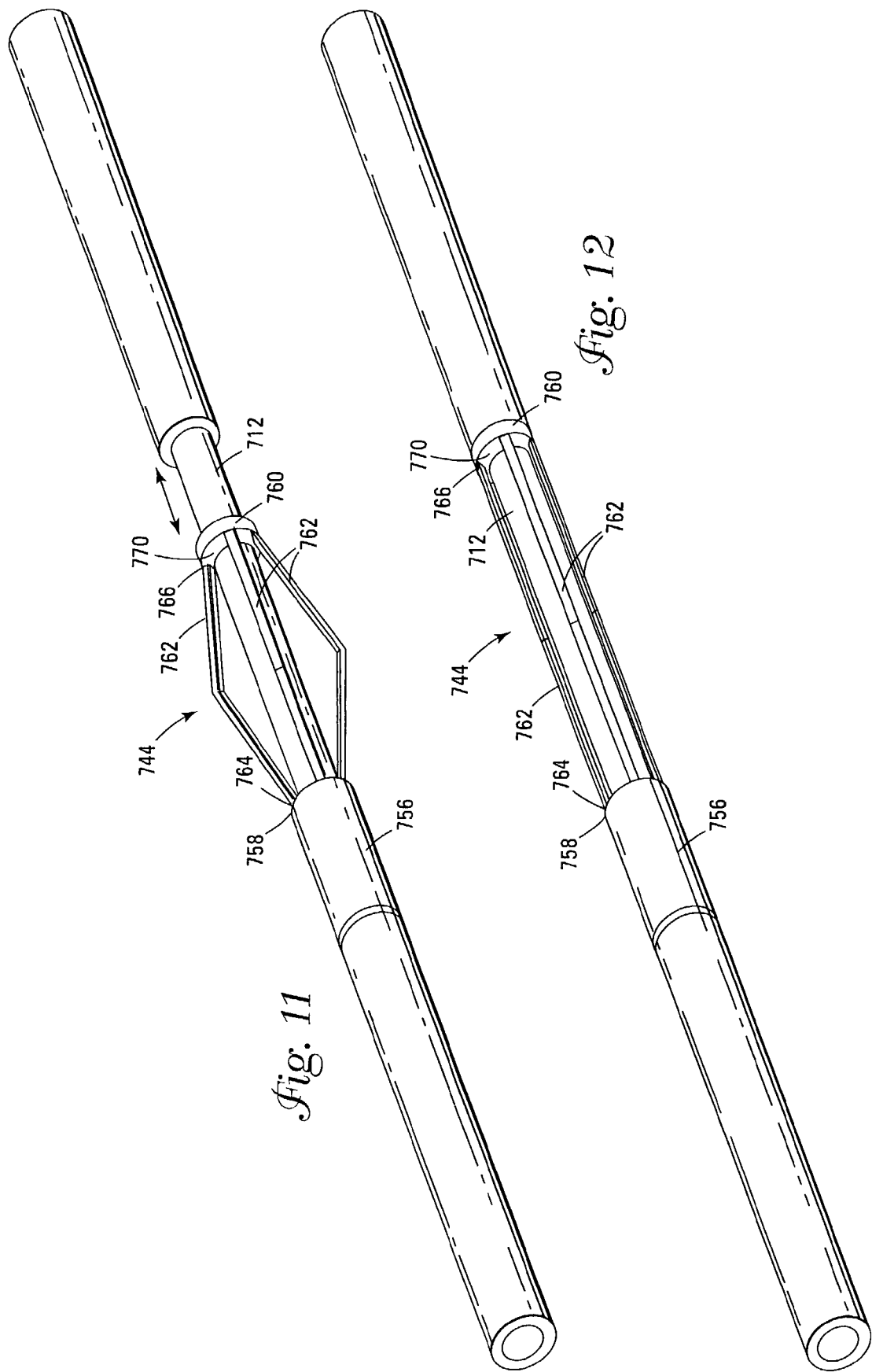

DEDICATED DISTAL PROTECTION GUIDEWIRES

FIELD OF THE INVENTION

The present invention pertains to guidewires for use in medical procedures. More specifically, the present invention relates to guidewires for use with embolic protection devices.

BACKGROUND OF THE INVENTION

Guidewires are frequently used to advance intraluminal devices such as stent delivery catheters, dilatation catheters or atherectomy catheters to a desired location within the vasculature. Such procedures typically involve the percutaneous introduction of an interventional device into the lumen of an artery or vein through a catheter or other delivery device.

One specific application guidewires are employed is the placement of a therapeutic device in a patient's vascular system to perform percutaneous transluminal coronary angioplasty (PTCA). In a typical PTCA procedure, a guidewire is introduced through a guide catheter and is advanced through the vasculature to a point distal a lesion. Once the guidewire is in position, a dilatation catheter having an inflatable balloon is advanced along the wire and positioned across the lesion to be dilated. The balloon is then inflated to a predetermined size, causing the lesion to become dislodged from the vessel walls. To prevent the vessel from subsequently reclosing upon removal of the device, or to prevent restenosis from developing over time, a stent can be advanced over the guidewire and placed across the site of the lesion.

During such procedures, it is not uncommon for embolic material such as atherosclerotic plaque to become dislodged from the wall of the artery or vessel, and flow downstream. To collect this dislodged material, an embolic protection filter can be used. These devices are typically placed on a distal section of a guidewire, and are mechanically actuated by struts that self-deploy within the vessel. A mesh screen attached to the device expands in a radial direction to collect the embolic material dislodged during the procedure.

Placement of embolic protection filters is generally accomplished in one of two ways. In one technique, the filter is directly attached to a distal portion of the guidewire prior to insertion in the body. The guidewire and accompanying filter are then inserted through a guide catheter and are placed at a desired location within the patient. Once in position, the guidewire can be used to slide the therapeutic device (e.g. an angioplasty catheter) to perform the procedure. In an alternative technique, a guidewire having a distal stop is first inserted into the patient, and then advanced to a desired location within the vessel. Once in position, the embolic protection filter and therapeutic device are then advanced along the guidewire to a site where the filter can subsequently capture the embolic debris.

Depending on the particular procedure to be performed, it may become necessary to advance multiple intravascular devices along the guidewire throughout the course of treatment. For example, in PTCA, it is not uncommon to exchange an occluded embolic protection filter with a new embolic protection filter should the filter mesh become saturated with embolic debris. When such an exchange is necessary, the movement of the filter and/or therapeutic device along the guidewire may cause the position of the guidewire to shift within the vessel, requiring the physician to re-position the guidewire. Furthermore, since relatively large outer diameters are often required to accommodate the filter and supporting catheter, the steering and tracking characteristics generally preferred in more conventional guidewires are often sacrificed in guidewires adapted for use with embolic protection devices.

SUMMARY OF THE INVENTION

The present invention pertains to guidewires for use in medical procedures. More specifically, the present invention relates to guidewires for use with embolic protection devices. In one embodiment of the present invention, a guidewire for use with an embolic protection filter comprises an elongated core wire having a proximal section and a distal section, a distal stop disposed about the distal section of the elongated core wire, and a proximal stop disposed about a portion of the elongated core wire proximal the distal stop.

The distal stop may be formed from an enlarged outer diameter portion of the core wire. Any number of suitable manufacturing processes can be utilized to form the distal stop, such as centerless grinding or turning on a lathe. Alternatively, the distal stop may be formed by bonding, crimping, soldering or otherwise attaching an object about a portion of the elongated core wire.

The proximal stop is configured to prevent proximal movement of an intravascular device along the guidewire in the absence of a force by the operator. In one exemplary embodiment, the proximal stop may comprise a polymeric member disposed about the elongated core wire. Examples of such polymeric members include an O-ring disposed about a recessed surface, and an annular ring having a plurality of circumferentially disposed notches.

In another embodiment of the present invention, a guidewire for use with an embolic protection filter comprises an elongated core wire having a proximal section and a distal section, a distal stop disposed about the distal section of the elongated core wire, a proximal stop disposed about a portion of the elongated core wire proximal the distal stop, and a wire coil. The wire coil may be comprised of one or more coil segments disposed about the distal section of the elongated core wire. Each coil segment may comprise a single wire strand helically disposed about the core wire. Alternatively, each coil segment may comprise a plurality of wire strands disposed about the core wire. A radiopaque material may be added to each coil segment to assist in placement of the guidewire within the body.

In yet another exemplary embodiment, a guidewire for use with an embolic protection filter may include an elongated core wire and a proximal stop, the proximal stop comprising a first tubular member, a second tubular member, and a plurality of struts attached therebetween. The first tubular member is fixedly attached to a portion of the elongated core wire. The second tubular member is slidably disposed along the elongated core wire distal the first tubular member. In use, the plurality of struts are actuatable between a collapsed position and a deployed position, the collapsed position permitting displacement of an intravascular device over the proximal stop, the deployed position preventing proximal displacement of the intravascular device over the proximal stop.

BRIEF DESCRIPTION OF THE DRAWINGS

FIG. 5 is a plan view of another proximal stop in accordance with an exemplary embodiment of the present invention, wherein the proximal stop comprises an annular ring having several circumferentially disposed notches;

FIG. 6 is a cross-sectional view of the distal section of a guidewire in accordance with another embodiment of the present invention, wherein the distal stop comprises a wire coil disposed about an enlarged diameter portion of the core wire, and wherein the proximal stop comprises a polymeric member;

FIG. 7 is a cross-sectional view of the distal section of a guidewire in accordance with another exemplary embodiment of the present invention having a polymeric coating;

FIG. 8 is a cross-sectional view of the distal section of a guidewire in accordance with yet another exemplary embodiment of the present invention, wherein a polymeric coating is disposed about the entire distal section of the guidewire;

FIG. 9 is a cross-sectional view of the distal section of a guidewire in accordance with another exemplary embodiment of the present invention, wherein the distal stop is formed by securing an object to a portion of the guidewire;

FIG. 10 is a cross-sectional view of the distal section of a guidewire in accordance with an alternative embodiment of the present invention, wherein the proximal stop is disposed about the elongated core wire between two wire coil segments;

FIG. 11 is a plan view of another proximal stop in accordance with the present invention, showing the proximal stop in an expanded position; and FIG. 12 is a plan view of the proximal stop mechanism illustrated in FIG. 11, showing the proximal stop in a collapsed position.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, materials and manufacturing processes are illustrated for the various elements, those skilled in the art will recognize that many of the examples provided have suitable alternatives that may be utilized.

Figure 1:
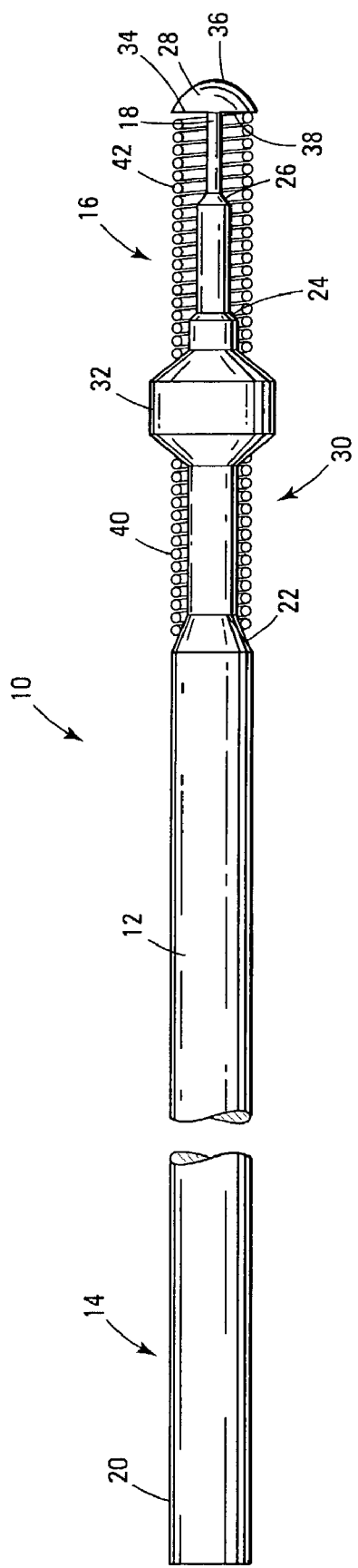
FIG. 1 is a plan view of guidewire for use with an embolic protection filter in accordance with an exemplary embodiment of the present invention.

FIG. 1 is a plan view of a dedicated distal protection guidewire in accordance with an exemplary embodiment of the present invention. Guidewire 10 includes an elongated core wire 12 having a relatively stiff proximal section 14, and a relatively flexible distal section 16. The distal section 16 of elongated core wire 12 is preferably tapered, having a smaller cross-sectional area at distal end 18 than at proximal end 20. In the exemplary embodiment shown in FIG. 1, elongated core wire 12 tapers to a smaller profile at points 22, 24 and 26. These tapered regions result in a guidewire having a relatively stiff proximal section 14 and a relatively flexible distal section 16 for improved maneuverability in the vasculature.

Distal section 16 of guidewire 10 further includes a coil tip 28, a wire coil 30, and a distal stop 32. Coil tip 28 is generally circular in cross-sectional area, and includes a proximal end 34 and a distal end 36. Distal end 36 of coil tip 28 is substantially round, and may include a hydrophilic coating for reduced tissue damage when advanced through the vasculature. The proximal end 34 of coil tip 28, in turn, is attached to the distal end 18 of elongated core wire 12, and includes a rearwardly facing shoulder 38 which abuts a portion of wire coil 30.

Wire coil 30 is comprised of a first wire coil segment 40 disposed proximal the distal stop 32, and a second wire coil segment 42 disposed distal the distal stop 32. In the exemplary embodiment shown in FIG. 1, the first and second wire coil segments 40, 42 are each formed of a single strand of wire helically disposed about a portion of the elongated core wire 12. In an alternative implementation (not shown), each of the wire coil segments 40, 42 may be formed of a plurality of wire strands disposed about a portion of elongated core wire 12. In either implementation, each of the wire coil segments 40, 42 are adapted to provide additional strength and radial flexibility to the distal end 16.

Guidewire 10 can be constructed of any suitable material (s) biocompatible with the body. Examples of suitable materials include 304 or 316 grade stainless steel, platinum, or nickel-titanium alloy (Nitinol). Nickel-titanium alloy exhibits super-elastic capabilities at body temperature (37°), which permits substantial bending or flexing of the guidewire with a relatively small amount of residual strain. It is anticipated, however, that other materials can be used.

A radiopaque material such as gold, platinum or tantalum can be added to the elongated core wire 12 and/or one or both of wire coil segments 40, 42, permitting the operator to fluoroscopically judge the placement of the guidewire 10 within the body. For example, coil segment 42 may be formed of a relatively high radiopaque material such as platinum, whereas coil segment 40 can be comprised of a relatively low radiopaque material such as stainless steel. When utilized in conjunction with a fluoroscopic monitor, the operator can more effectively gauge the location of the guidewire 10 within the vasculature.

Elongated core wire 12 can be formed using any number of suitable manufacturing processes such as centerless grinding (e.g. in-feed or end-feed grinding), or by turning on a lathe. In a centerless grinding technique, for example, the elongated core wire 12 can be constructed from a uniform diameter stainless steel wire that is centerless ground along the distal section 16 to form a tapered surface. The distal stop 32 may be formed by leaving intact a portion of the core wire 12 while grinding the distal section 16 of the guidewire 10 to a desired thickness. Moreover, the length and diameter of guidewire 10 can be varied, depending on the particular location within the body to be traversed, and depending on the size of the intravascular device to be advanced thereon. In addition, the outer diameter of the distal and/or proximal stops can be varied. In one particular implementation, the distal stop may have an outer diameter of at least 0.018 inches.

Figure 2:
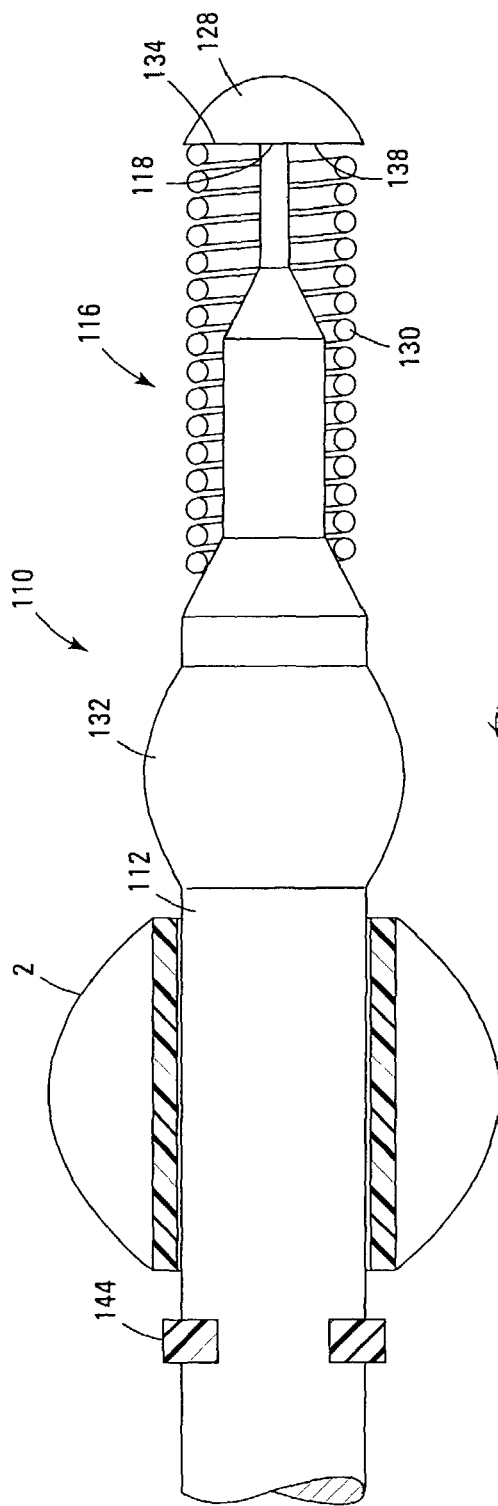
FIG. 2 is a cross-sectional view of the distal section of a guidewire in accordance with an alternative embodiment of the present invention, wherein the guidewire includes a proximal stop.

FIG. 2 illustrates an alternative embodiment of a guidewire for use with an embolic protection filter in accordance with the present invention. Guidewire 110 includes an elongated core wire 112 having a proximal section (not shown), and a distal section 116. Distal section 116 of guidewire 110 includes a coil tip 128 and a distal stop 132, similar to that described with respect to the embodiment of FIG. 1. A wire coil 130 comprising a single wire coil segment is located distal the distal stop 132, and abuts shoulder 138 disposed on the proximal end 134 of coil tip 128.

Guidewire 130 further includes a proximal stop 144 disposed about a portion of core wire 112 proximal distal stop 132. Proximal stop 144 is configured to deform when an intravascular device 2 such as the embolic protection filter illustrated in FIG. 2 is advanced thereon by the operator. Intravascular device 2 has an inner diameter that is slightly smaller than the outer diameter of the proximal stop 144. When the operator exerts a sufficient force on the proximal stop 144 by advancing the intravascular device 2 distally along the guidewire 110, the proximal stop 144 bends slightly, allowing the intravascular device 2 to be advanced beyond the proximal stop 144. Once the intravascular device 2 is distal the proximal stop 144, the proximal stop 144 returns to its original position, as shown in FIG. 2. When utilized in conjunction with distal stop 132, proximal stop 144 constrains movement of the intravascular device 2 to a particular location along the guidewire 110.

In the exemplary embodiment of FIG. 2, proximal stop 144 is comprised of a polymeric member disposed about and secured to a portion of the elongated core wire 112. In one particular implementation, the proximal stop 144 may include an O-ring 146 having outer diameter slightly larger than the inner diameter of the intravascular device 2. O-ring 146 may be comprised of an elastomeric material such that it resumes its original shape when the deforming force is removed. Examples of suitable elastomeric materials include polyurethane, nitrile, neoprene, ethylene-polypropylene (EPDM), natural rubber, synthetic polyisoprene, butadiene-styrene (Buna S), butadiene-acrylonitrile (Buna N), polychloroprene, fluorosilicone or silicon rubber. In use, the O-ring 146 prevents proximal motion of the intravascular device along the guidewire 110 in the absence of a force exerted by the operator.

Figure 4:
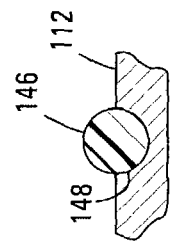
FIG. 4 is a cross-sectional view of the proximal stop in FIG. 3, showing the O-ring disposed within a recessed surface on the guidewire.

A recess 148 disposed on the outer diameter of elongated core wire 112 can be utilized to secure the O-ring 146 to the elongated core wire 112, as shown in FIG. 4. Recess 148 is substantially circular in shape, and has a radius of curvature that corresponds with the shape of the O-ring 146. While the recess 148 shown in FIG. 4 is substantially circular in shape, it is contemplated that other shaped surfaces can be used. For example, recess 148 may be a gland (i.e. rectangular in shape) to permit a portion of the O-ring 146 to deform therein when compressed. Furthermore, it is contemplated that the dimensions of the O-ring 146 can be selected to correspond with the particular shape and size of the guidewire and intravascular device employed.

Figure 3:
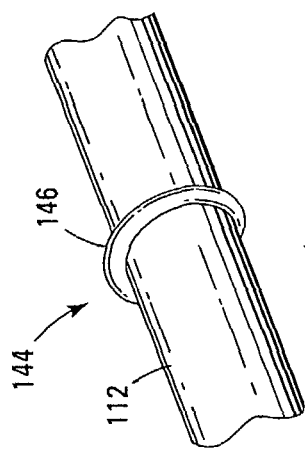
FIG. 3 is a plan view of a proximal stop in accordance with an exemplary embodiment of the present invention, wherein the proximal stop comprises an O-ring.

In a similar implementation illustrated in FIG. 5, proximal stop 144 may include an annular ring 150 having a plurality of circumferentially disposed notches 152. As with the O-ring shown in FIGS. 3-4, annular ring 150 has an outer diameter that is slightly larger than the inner diameter of the intravascular device 2, and may include an elastomeric material to facilitate bending. In use, the circumferential notches 152 are configured to allow the outer portion of the annular ring 150 to bend and permit movement of the intravascular device 2 thereon.

As with any of the other proximal stop mechanisms discussed herein, annular ring 150 may comprise a material having certain compressability, hardness and elasticity characteristics suited for use with a particular intravascular device or guidewire. For example, annular ring 150 may be formed of an elastomeric material having a relatively low modulus of elasticity to permit substantial bending. In other applications where greater resistance to bending is desired, an elastomeric material having a relatively high modulus of elasticity may be used. Other interrelated factors such as the hardness and compressability may also be selected, depending on the particular application.

FIG. 6 illustrates an alternative embodiment of a guidewire 210 in accordance with the present invention. Guidewire 210 includes an elongated core wire 212 having a proximal section (not shown), a distal section 216, and a coil tip 228. Guidewire 210 further includes a distal stop 232 formed by an enlarged diameter portion of elongated core wire 212, and a proximal stop 244. As with the previous embodiments, a coil tip 228 is attached to the distal end 218 of elongated core wire 212.

Guidewire 210 further includes a wire coil 230 comprising a single wire coil segment helically disposed about a portion of the distal section 216. As shown in FIG. 6, wire coil 230 extends along the core wire 212 from a point distal the proximal stop 244 to the proximal end 234 of coil tip 228. In use, the portion 252 of the wire coil 230 located adjacent to distal stop 232 prevents movement of an intravascular device beyond the distal stop 232.

Proximal stop 244 comprises a polymeric member disposed about a portion of distal section 216 proximal wire coil 230. Similar to proximal stops described with respect to FIGS. 2-5, proximal stop 244 is configured to bend and permit movement of an intravascular device thereon when a sufficient force is exerted by the operator. The proximal stop 244 may be set within a recessed surface (not shown) to prevent the proximal stop 244 from sliding along the elongated core wire 212 during advancement of the intravascular device. Moreover, other factors such as the hardness, elasticity, and compressability of the proximal stop 244 may be selected, if desired, to function with particular guidewires and intravascular devices.

FIG. 7 illustrates yet another exemplary embodiment of a guidewire 310 in accordance with the present invention, wherein the distal section 316 of the guidewire 310 includes a polymeric coating 350. Guidewire 310 comprises an elongated core wire 312 having a proximal section (not shown), and a distal section 316. Guidewire 310 also includes a coil tip 328 disposed on the distal end 318 of core wire 312, a distal stop 332, and a proximal stop 344. Disposed about core wire 312 distal the distal stop 332 and proximal the distal end 318 of core wire 312 is a wire coil 330, similar to that depicted in FIG. 2.

Guidewire 330 further includes a polymeric coating 350 disposed about a portion of the elongated core wire 312 and the proximal stop 344. Polymeric coating 350 can be made any number of suitable polymeric materials, including polytetrafluoroethylene, polypropylene, polyurethane, polyamide polyethylene, and polyethylene terephthalate. When applied to the guidewire 310, polymeric coating 350 provides a relatively smooth, lubricious surface, facilitating movement of an intravascular device along the wire.

Although the guidewire 310 of FIG. 7 includes a polymeric coating 350 over only a portion of the distal section 316, other arrangements are contemplated. As shown in FIG. 8, for example, a distal protection guidewire 410 in accordance with the present invention can include a polymeric coating 450 disposed about the entire distal section 416 of elongated core wire 412, including proximal stop 444 and distal stop 432. As with guidewire 310, the distal end 418 of the elongated core wire 412 abuts the proximal end 434 of coil tip 428.

To facilitate advancement of the intravascular device about the proximal stops 344, 444, the hardness and compressability of the polymeric coating 350, 450 can be varied. In some applications, for example, the durometer hardness of the polymeric coating 350, 450 may be relatively low to permit sufficient deformation when the intravascular device is advanced. In other applications where significant deformation is not required, the durometer hardness of the polymeric coating 350, 450 may be much greater.

FIG. 9 illustrates another embodiment of a guidewire 510 in accordance with an exemplary embodiment of the present invention, wherein a distal stop 532 is formed by securing an object about a portion of the distal section 516 of guidewire 510. Guidewire 510 includes an elongated core wire 512 having a proximal section (not shown), a distal section 516, a coil tip 528, a wire coil 530, and a proximal stop 544. A distal stop 532 is formed about a portion of distal section 516 by securing an object about wire coil 530. Distal stop 532 comprises an object having an outer diameter slightly larger than the inner diameter of the intravascular device, thus preventing distal movement of the intravascular device along the guidewire 510 distal the distal stop 532.

Attachment of distal stop 532 to the guidewire 510 may be accomplished by any number of attachment means, including crimping, soldering, brazing, bonding, or any combination thereof. Furthermore, distal stop 532 may be formed by any number of materials, such as stainless steel or nickel-titanium alloy. In one particular implementation, distal stop 532 may be formed by heat bonding a polymeric object to the wire coil 530 and/or the elongated core wire 512.

Guidewire 510 further includes a proximal stop 544 disposed about a portion of wire coil 530 proximal the distal stop 532. Proximal stop 544 is adapted to deform when an intravascular device is advanced thereon by the operator. As with other embodiments discussed herein, the elasticity, compressability and hardness of the proximal stop 544 may be selected depending on the particular type of guidewire and/or intravascular device to be employed.

In a similar embodiment illustrated in FIG. 10, a guidewire 610 may include a proximal stop 644 disposed about the elongated core wire 612. Guidewire 610 includes a first wire coil segment 640, a second wire coil segment 642, and a distal stop 632. Unlike the embodiment illustrated in FIG. 9, however, proximal stop 644 is directly secured to a portion of the elongated core wire 612. Attachment of the proximal stop 644 to the elongated core wire 612 may be accomplished by crimping, soldering, brazing, bonding, or any combination thereof. In use, the proximal stop 644 is adapted to deform when an intravascular device is advanced thereon.

Referring now to FIGS. 11-12, a guidewire having an actuatable proximal stop 744 will now be described. As shown in FIG. 11, proximal stop 744 comprises a first tubular member 756 secured to the elongated core wire 712, a second tubular member 760 slidably disposed about elongated core wire 712 distal the first tubular member 756, and a plurality of struts 762 attached therebetween. The proximal end 764 of each strut 762 is attached to a distal end 758 of the first tubular member 756. The distal end 766 of each strut 762, in turn, is attached to a proximal end 770 of the second tubular member 760. The plurality of struts 762 are actuatable between a collapsed position and a deployed position, the collapsed position permitting displacement of an intravascular device over the proximal stop 744, the deployed position preventing proximal displacement of the intravascular device over the proximal stop 744.

To attach the proximal stop 744 to the guidewire, each of the tubular members 756, 760 can be formed by bonding two split tubular halves about the core wire 712 to form a single tubular member. Materials suitable for such purpose include polytetrafluoroethylene, polyethylene, polypropylene, and/or polyvinylchloride. In an alternative implementation, each of the tubular members 756, 760 can be formed by soldering about elongated core wire 712 two split tubular halves made from a metal such as nickel-titanium alloy. Bonding of the metal halves can be accomplished by soldering, brazing, welding or otherwise securing the tubular members 756, 760 to the elongated core wire 712.

In use, an intravascular device such as an embolic protection filter can be advanced along the guidewire 712 to a point proximate the proximal stop 744. Continued advancement of the device over the expandable struts 762 causes the second tubular member 760 to slide distally, forcing the expandable struts 762 to radially collapse, as shown in FIG. 12. Once the intravascular device is advanced distal the second tubular member 760, proximal stop 744 prevents the intravascular device from sliding proximally. If the intravascular device is retracted over the proximal stop 744, the second tubular member 760 slides proximally towards the first tubular member 756, forcing the expandable struts 762 to radially expand. With the expandable struts 762 in a radially expanded (i.e. deployed) position, the intravascular device is prevented from further retracting proximally along the guidewire 710.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. Changes may be made in details, particular in matters of shape, size and arrangement of parts without exceeding the scope of the invention. For example, the location of the proximal and distal stops may be altered, and the materials used to form the core wire and the wire coil can be varied, depending on the particular application. It will be understood that this disclosure is, in many respects, only illustrative.

What is claimed is:

1. A guidewire for use in a medical procedure, comprising:
   an elongated core wire having a proximal section and a distal section;
   a distal stop disposed about the distal section of said elongated core wire, the distal stop comprising an enlarged outer diameter portion of the elongated core wire; and
   a proximal stop fixed to and about a portion of said elongated core wire proximal the distal stop, the proximal stop comprising a polymeric member configured to deform when an intravascular device is advanced thereon.

2. The guidewire of claim 1, further comprising a wire coil disposed about a portion of said distal section.

3. The guidewire of claim 2, wherein said wire coil is helically disposed about said distal section.

4. The guidewire of claim 2, wherein said wire coil is comprised of a single coil segment.

5. The guidewire of claim 2, wherein said wire coil is comprised of two or more coil segments.

6. The guidewire of claim 2, wherein said wire coil is formed of a stainless steel material.

7. The guidewire, of claim 2, wherein said wire coil is formed of a shape-memory material.

8. The guidewire of claim 7, wherein said shape-memory material is nickel titanium alloy.

9. The guidewire of claim 2, wherein said wire coil includes a radiopaque material.

10. The guidewire of claim 1, wherein said distal stop is formed from an object disposed about and secured to a portion of the elongated core wire.

11. The guidewire of claim 1, wherein the outer diameter of said distal stop is at least 0.018 inches.

12. The guidewire of claim 1, further comprising a polymeric coating on at least a portion of said distal section.

13. The guidewire of claim 12, wherein said polymeric coating comprises polytetrafluoroethylene.

14. The guidewire of claim 1, wherein said polymeric member is an annular object having a plurality of circumferentially disposed notches.

15. The guidewire of claim 1, wherein said polymeric member is an O-ring.

16. The guidewire of claim 1, wherein said intravascular device is an embolic protection filter.

17. The guidewire of claim 1 further comprising a wire coil disposed about a portion of said distal section.

18. The guidewire of claim 17, wherein said wire coil is helically disposed about said distal section.

19. The guidewire of claim 17, wherein said wire coil is comprised of a single coil segment.

20. The guidewire of claim 17, wherein said wire coil is comprised of two or more coil segments.

21. The guidewire of claim 17, wherein said wire coil is formed of a stainless steel material.

22. The guidewire of claim 17, wherein said wire coil is formed of a shape-memory material.

23. The guidewire of claim 22, wherein said shape-memory material is nickel titanium alloy.

24. The guidewire of claim 17, wherein said wire coil includes a radiopaque material.

25. The guidewire of claim 17, wherein said distal stop is formed from an object disposed about and secured to a portion of the elongated core wire.

26. The guidewire of claim 17, wherein the outer diameter of said distal stop is at least 0.018 inches.

27. The guidewire of claim 17, further comprising a polymeric coating on at least a portion of said distal section.

28. The guidewire of claim 27, wherein said polymeric coating comprises polytetrafluoroethylene.

29. The guidewire of claim 17, wherein said proximal stop is an annular object having a plurality of circumferentially disposed notches.

30. The guidewire of claim 17, wherein said proximal stop is an O-ring.

31. The guidewire of claim 17, wherein said intravascular device is an embolic protection filter.

32. A guidewire for use in a medical procedure, comprising:
   an elongated core wire having a proximal section and a distal section;
   a distal stop disposed about the distal section of said elongated core wire, the distal stop comprising an enlarged outer diameter portion of the elongated core wire; and
   a proximal stop fixed to and about the distal section of said elongated core wire proximal the distal stop, the proximal stop comprising a polymeric member configured to deform when an intravascular device is advanced thereon.

* * * * *